United States Patent [19]

Gururaja et al.

[11] Patent Number: 5,625,149
[45] Date of Patent: Apr. 29, 1997

[54] ULTRASONIC TRANSDUCTOR

[75] Inventors: Turukevere R. Gururaja, North Andover; Larry A. Ladd, Methuen, both of Mass.

[73] Assignee: Hewlett-Packard Company, Palo Alto, Calif.

[21] Appl. No.: 281,323

[22] Filed: Jul. 27, 1994

[51] Int. Cl.$^6$ .......................... G01N 29/00; H01L 41/08; A61B 8/14; H04R 17/00
[52] U.S. Cl. .......................... 73/632; 310/358; 310/334; 310/364; 310/366; 128/662.03; 367/162
[58] Field of Search .............................. 73/632; 310/334, 310/358, 364, 366, 800; 29/25.35; 128/662.03; 367/155, 157, 162

[56] References Cited

U.S. PATENT DOCUMENTS

| | | | |
|---|---|---|---|
| 4,963,782 | 10/1990 | Bui et al. | 310/358 |
| 5,115,809 | 5/1992 | Saitoh et al. | 128/662.03 |
| 5,239,736 | 8/1993 | Sliwa, Jr. et al. | 29/25.35 |
| 5,359,760 | 11/1994 | Busse et al. | 29/25.35 |
| 5,392,259 | 2/1995 | Bolorforosh | 367/152 |

OTHER PUBLICATIONS

M.I. Haller, et al. "Tapered Acoustic Matching Layers" Nov. 1993.
M.I. Haller, et al. "Micromachined Acoustic Matching Layers" Jul. 1992.
J.D. Larson III, "An Acoustic Transducer Array For Medical Imaging" Oct. 1983.
M.I. Haller, et al. "Micromachined Ultrasonic Materials" 1991.
Aero-Tech Reports "One-Quarter Wavelength Theory and Application" 1978.
Aero-Tech Reports "Multiple Matching Layer Theory and Application" 1980.
P.C. Pedersen, et al. "Impedance Matching Properties of an Inhomogeneous Matching Layer with Continuously Changing Acoustic Impedance" Apr. 1982.
T.R. Gururaja, "Piezoelectric Transducers for Medical Ultrasonic Imaging" Sep. 1992.
SPIE, "New Developments in Ultrasonic Transducers and Transducer Systems" Jul. 1992.
W.A. Smith, "Composite Piezoelectric Materials for Medical Ultrasonic Imaging Transducers" 1986.

Primary Examiner—Hezron E. Williams
Assistant Examiner—Richard A. Moller
Attorney, Agent, or Firm—Jonathan B. Penn

[57] ABSTRACT

A multilayer composite transducer is disclosed. The multilayer composite transducer comprises a plurality of layers wherein a piezoelectric material is dispersed periodically within a polymer matrix. The piezoelectric material is typically formed into columns or slabs, and these columns and slabs need to be aligned from one layer to the next. As this alignment can be difficult to perform, the present invention teaches a first method for fabricating the multilayer composite transducer which allows the alignment to be easily accomplished and a second and third method which reduce or eliminate the need for the alignment.

20 Claims, 3 Drawing Sheets

ULTRASONIC TRANSDUCTOR

BACKGROUND OF THE INVENTION

This invention relates to the field of ultrasonics. Within that field, the invention relates to ultrasonic transducers.

The use of ultrasound in both non-invasive medical testing and diagnosis and the non-destructive testing of mechanical assemblies such as engines and bridges is known, as are systems which generate and analyze ultrasonic signals. The basic components of an ultrasonic diagnostic system are an electrical signal generator, a transducer which converts the electrical signal into an ultrasonic signal and which receives the reflected ultrasonic signal, and a processor for analyzing the reflected ultrasonic signal.

In medical ultrasonic testing and diagnosis, the most common piezoelectric material used to fabricate ultrasonic transducers is lead zirconate titanate ("PZT"), which is a ceramic material. PZT is used because it has a relatively high piezoelectric coupling constant. Unfortunately, PZT based materials have a relatively large acoustic impedance (30 Mrayl) as compared to the human body (1.5 Mrayl). This large difference in acoustic impedance makes coupling ultrasonic energy from a PZT material into a human body very inefficient. To improve coupling efficiency, transducers are commonly fabricated with one or more matching layers between the PZT ceramic and the human body to improve the coupling and transmission of ultrasonic energy.

The aim is to obtain a proper broad band impulse response.

Substantial efforts have been made to reduce the acoustic impedance of piezoelectric materials by fabricating a composite material made from PZT ceramic and a low acoustic impedance polymer. FIGS. 1a through 1d illustrate several proposed PZT/composite transducer configurations. Composites with a 1-3 connectivity, shown in FIG. 1a, consist of square or circular PZT posts or fibers embedded periodically or randomly in a polymer matrix. A 2-2 composite, shown in FIG. 1b, consists of alternate slabs of PZT and polymer arranged in a periodic manner. A 3-3 composite, shown in FIG. 1c, is made of three dimensional, interconnected porous PZT impregnated with a polymer matrix. A 0-3 composite, shown in FIG. 1d, consists of piezoelectric material in a powder form dispersed throughout a polymer matrix. In each of these examples, the acoustic impedance is substantially lower than that of single phase PZT ceramic and is dependent on the volume percent of PZT used in the composite.

Another constraint on transducer design is the need to match the electrical impedance of the system's electronics and the transducer array. Linear and phased array transducers which are widely used for real-time ultrasonic imaging in biomedical and non-destructive testing applications consist of a one dimensional array of narrow (~100 to ~600 micrometers wide) transducer elements. The fine geometry of the array elements results in the individual elements having a relatively low capacitance. The long cables used to couple the transducer to the system become a very large capacitive load in comparison with the individual elements and result in a poor electrical impedance match between the system's electronics, which includes the cable, and the array elements. Better matching of the electrical impedance of the transducer elements with the combined electrical impedance of the cable and system electronics is desirable.

The use of a composite material in a linear or phased array improves the acoustic matching of the array but, as the dielectric constant of the composite material is lower than that of the PZT ceramic, it simultaneously worsens the electrical impedance match between the system and the array. As the volume percent of polymer in the transducer's composite material increases, the severity of this problem increases. Both the acoustic and electrical impedance matches must be optimized simultaneously to obtain a compact pulse and a relatively wide band response from the transducer.

A known method for improving electrical impedance matching in transducer arrays fabricated with ceramic materials is to construct a multilayer ceramic transducer as shown in FIG. 2. Transducer 30 is comprised of several layers 31 of PZT. Electrodes 32 are placed between layers 31. These electrodes are coupled to external electrodes 39 and 37 alternatively, the electrode between the first two layer being coupled to external electrode 39, the electrode between the next two layers being coupled to electrode 37, and so on. The small insulating beads 35 keep internal electrodes 32 from contacting the wrong external electrode. This technique of increasing the electrical impedance of a ceramic transducer has been used in the ceramic capacitor industry. An N layer multilayer transducer with the same final thickness as a given baseline transducer will have a capacitance which is $N^2$ more than the capacitance of the single layer transducer. For example, a two layer multilayer transducer has four times the capacitance of a single layer transducer. Using this type of multilayer configuration makes matching the electrical impedance between the system and transducer easier.

Unfortunately, multilayer ceramic transducer 30's material design is not acoustically optimal, as it has the same poor acoustical match to the human body as does a single layer ceramic transducer.

A transducer which can more closely match the acoustic impedance of the human body and simultaneously closely match the electrical impedance of the system is therefore needed.

SUMMARY OF THE INVENTION

The present invention comprises a multilayer composite transducer and several methods for fabricating it. An N layer multilayer composite transducer exhibits an increased effective dielectric constant and provides better electrical impedance matching, as well as improved acoustic matching. It should be noted that although the present invention only discusses impedance matching with a human body, nothing herein should be taken to limit the present invention to that environment or use only. The teachings herein could be used to fabricate a transducer which would be acoustically matched with any other object undergoing non-intrusive inspection.

Each layer in the multilayer transducer is a piezoelectric/polymer composite. Although the most commonly used piezoelectric material is a PZT ceramic, nothing herein restricts the present invention to only that material. Any piezoelectric or electrostrictive material could be used instead of PZT. All references in the specification and claims to PZT should be taken to include these other piezoelectric and electrostrictive materials.

The PZT material in each layer will typically be formed into posts or slats, which respectively have 1-3 and 2-2 connectivity. As the PZT elements of the present invention are formed as posts or slats, misalignment between the posts or slats in adjacent layers of the multilayer transducer can and does result in undesired resonance nodes, as well as reduced sound velocity and a lower resonant frequency. The variable amount of layer to layer misalignment in multilayer composite transducers results in considerable variation in performance from transducer to transducer. Aligning the individual layers of composite material accurately is a difficult task and not desirable in a production process.

The present invention teaches three methods for making composite multilayer transducers which do not have undesired resonance modes or variations in resonant frequency due to misalignment between the layers. The first method uses very fine pitch composite materials. If the composite pitch of each composite layer is less. than about 0.7 of the layer's thickness, the undesired modes are reduced in amplitude. If the composite pitch is less than 0.35 of the layer's thickness, then no undesired modes occur, regardless of how the layers are aligned or misaligned. This is explained by the composite pitch being considerably finer than the wavelength of ultrasound at the frequency of operation. Using fine pitch composite layers eliminates the need for aligning the layers.

In the second method for making a composite multilayer transducer taught by the present invention, a thin layer of electrically conducting, mechanically rigid material is sandwiched between layers of PZT/polymer composite material. The rigid material forces each layer of PZT/polymer composite material to move as a rigid body and normalizes the vibration differences between the polymer and PZT at the interface.

The third method taught by the present invention fabricates the transducer by injection molding the 1-3 or 2-2 composite structure with a thin base material holding the posts or slats. A thin layer of platinum or other noble metal ink is screened onto the base material. Two such injection molded parts can then be sintered together to create a multilayer structure. The injection molding process insures that the PZT elements are in exactly the same location in each layer, making their alignment straightforward.

These embodiments will now be described in detail with reference to the figures listed and described below.

DETAILED DESCRIPTION OF THE PREFERRED EMBODIMENTS

Figure 1A:
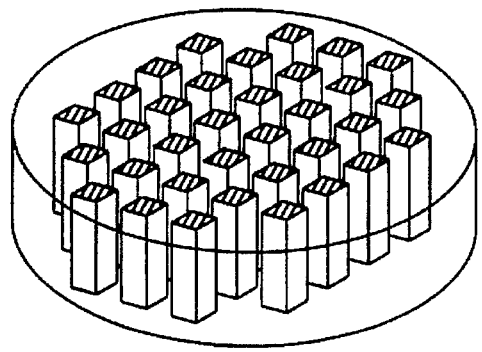
FIGS. 1a, 1b, 1c, and 1d show PZT/polymer composite transducers with various different connectivities (Prior Art)
Figure 1B:
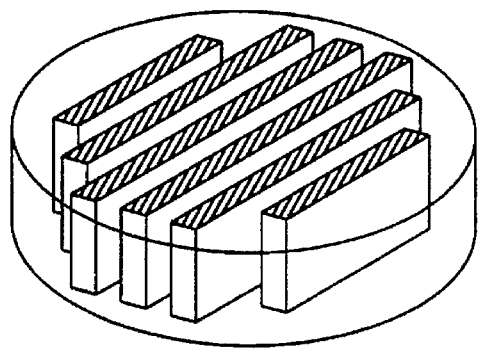
Figure 1C:
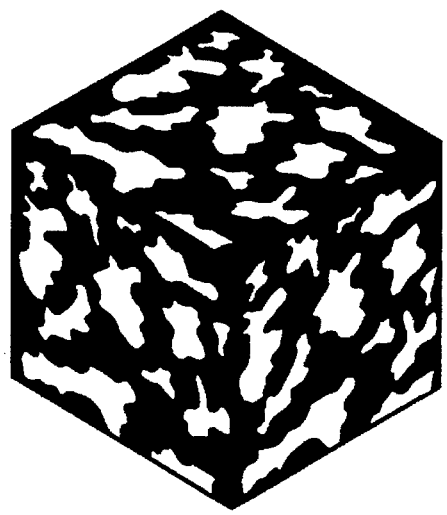
Figure 1D:
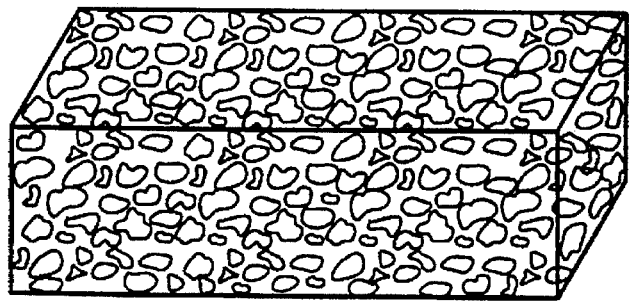
Figure 2:
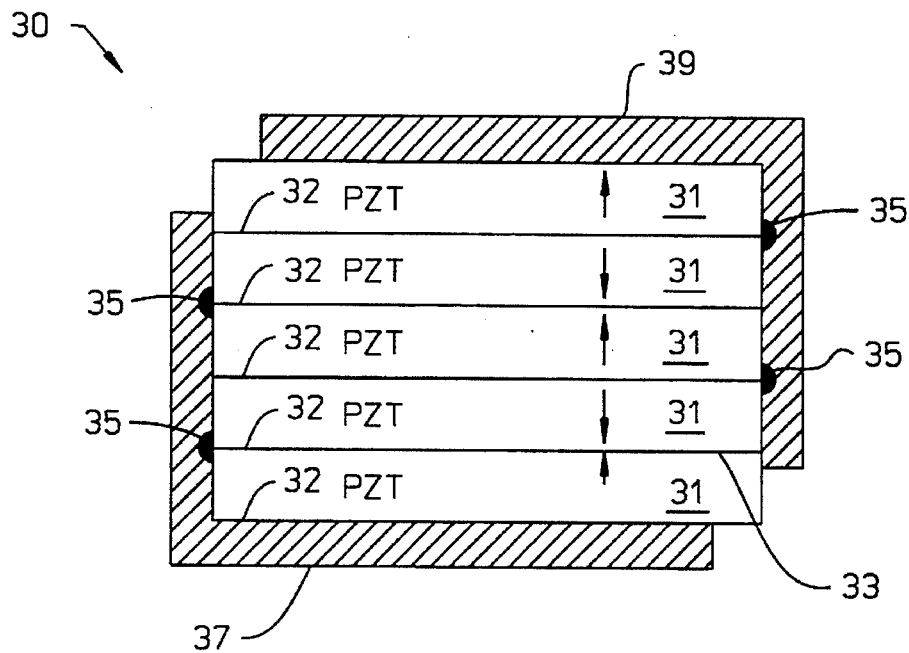
FIG. 2 illustrates a known PZT ceramic multilayer transducer(Prior Art)
Figure 3:
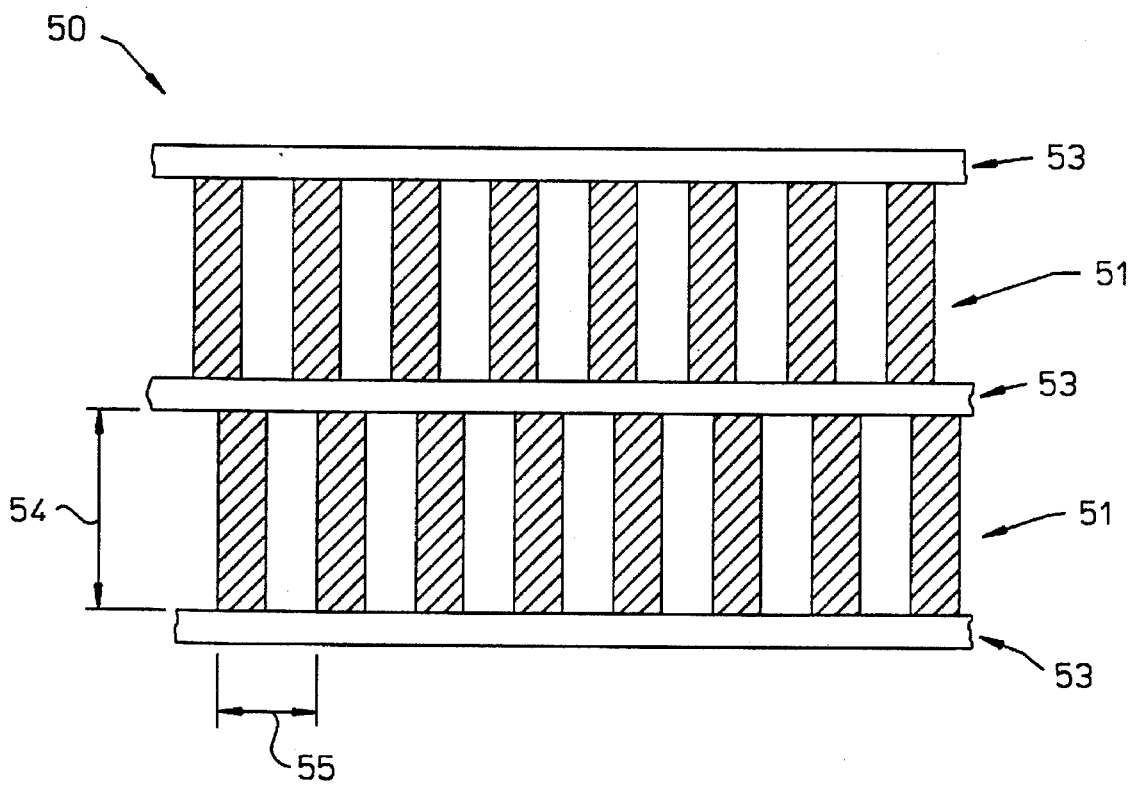
FIG. 3 illustrates a composite multilayer transducer fabricated using a first method.

A multilayer composite transducer fabricated using the first method taught by the present invention is shown in FIG. 3. A PZT/polymer composite transducer 50 is comprised of a plurality of layers 51, each layer comprised of a PZT/polymer composite. The overall structure could be similar to the multilayer ceramic transducer illustrated in FIG. 2. For clarity, only two layers are illustrated in FIG. 3. Electrodes 53 are placed between layers 51 and on the top and bottom of transducer 50.

As shown in FIG. 3, the PZT material is formed into slabs or posts, which result in a multilayer composite transducer of 1-3 or 2-2 connectivity. The pitch 55 of the posts or slabs is the distance from center to center of the posts or slabs. The thickness 54 of a layer is equal to the height of the slabs or posts. The ratio of the pitch to the thickness (pitch/thickness) must be less than 0.7 in this embodiment. If the ratio is further reduced to 0.35, the acoustic properties of the transducer will not be affected by the alignment of the layers. For ratios between 0.7 and 0.35, the effects of misalignment are reduced and performance is only slightly degraded.

Figure 4:
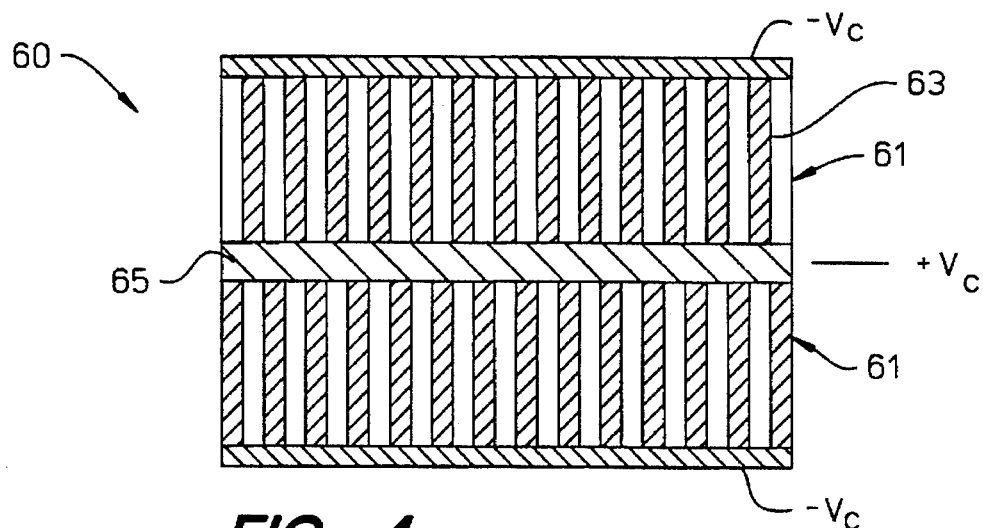
FIG. 4 shows a composite multilayer transducer fabricated using a second method.

The second embodiment of the present invention is shown in FIG. 4. In this embodiment, the requirement for alignment of the PZT elements across the layers is also eliminated. In transducer 60, the PZT elements 63 are not perfectly aligned. However, by inserting a thin layer 65 of an electrically conducting, mechanically rigid material having the same acoustic impedance as the PZT/polymer composite material between layers 61 of the PZT/polymer composite material, the need for perfect alignment is eliminated. Layer 65 can be comprised of a single- or multi-phase material and the layer integrates the acoustic pulses at the two interfaces. The rigid material of layer 65 forces each layer 61 of PZT and polymer columns to move as a rigid body. This normalizes the vibration differences between the polymer and PZT at the interface. Layer 65 can be comprised of a carbon fiber reinforced composite material produced to have the same impedance as the PZT/polymer composite material. Carbon fiber reinforced composites have a very fine internal structure and could serve as stiff normalizing layers. The thickness of layer 65 must be only a small fraction of the wavelength at the operating frequency in the transducer.

Figure 5:
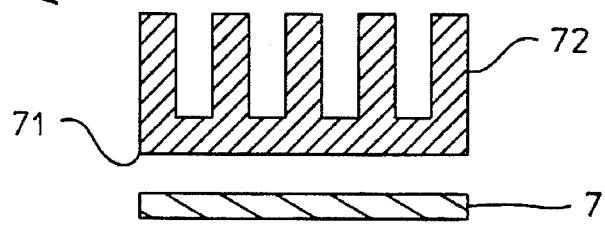
FIG. 5 illustrates the third method for fabricating a multilayer composite transducer taught by the present invention.
Figure 5:
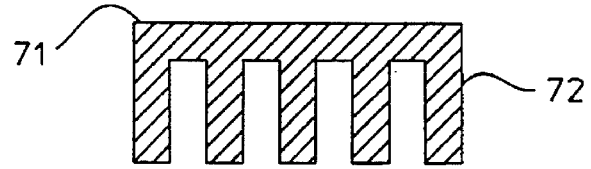
Figure 6:
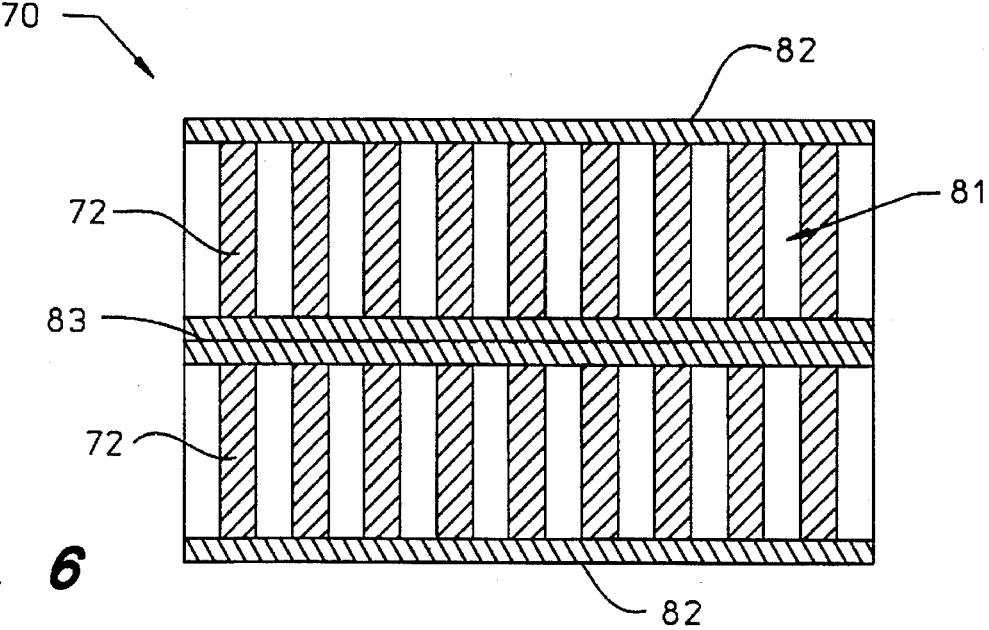
FIG. 6 further illustrates the third method of the present invention.

The third method taught by the present invention for fabricating a multilayer composite transducer is shown in both FIGS. 5 and 6. As shown in FIG. 5, transducer 70 is fabricated injection molded piezoelectric parts. These parts comprise a thin baseplate 71 which has posts or slabs 72 fabricated on one side. A conductive ink 73 coats the outside of baseplate 71 and two baseplates are sintered together with the inked sides abutting one another.

The completed multilayer composite transducer 70 fabricated using this third method is shown in FIG. 6. The voids between the posts or slats of the baseplates are filled with a polymer 81 to make a low acoustic impedance polymer structure. The transducer can then be lapped or ground to the desired thickness and external electrode 82 can be attached to the top and bottom of transducer 70 and external electrodes can be attached to the center electrode 83. Transducer 70 will not have unwanted resonances due to misaligned posts or slabs as the injection molded parts can be made to very close tolerances, the layers can be easily aligned before sintering, and, even if the posts and slabs are not perfectly aligned, the central layer formed from the conductive ink will normalize the vibrations between the layers. This third method thus also eliminate unwanted resonance modes and is easy to manufacture.

What is claimed is:

1. An ultrasonic transducer comprising:

a plurality of first layers, the first layers comprising a composite of a piezoelectric material and a low acoustic impedance material;

a plurality of internal electrodes, a first internal electrode overlying a first layer and successive internal electrodes overlying successive first layers; and a first and second external electrode, a first internal electrode being coupled to the first external electrode and a second internal electrode being coupled to the second external electrode, successive internal electrodes being coupled alternatively to the first and second external electrodes.

2. The ultrasonic transducer of claim 1 wherein the piezoelectric material of the first layers is formed by injection molding and the first layers and the internal electrodes are laminated together by sintering to form the transducer.

3. The ultrasonic transducer of claim 1 wherein a plurality of second layers are placed between the first layers, the second layers comprising electrically conductive and mechanically rigid material, the first layers, the second layers and the internal electrodes being laminated together to form the transducer.

4. The ultrasonic transducer of claim 1 wherein the piezoelectric material in the first layer is formed as a plurality of structures, each structure having the shape of one of slabs and posts, the distance between the centers of adjacent structures defining a pitch, the height of the structures defining a thickness, the ratio of the pitch divided by the thickness being less than 0.7.

5. The ultrasonic transducer of claim 4 wherein the ratio is less than 0.35.

6. The ultrasonic transducer of claim 1 wherein the piezoelectric material in the first layers is formed into a plurality of columns, the columns being evenly distributed within the low acoustic impedance material, and the columns in each of the first layers being in alignment when the first layers form the transducer.

7. The transducer of claim 1 wherein the piezoelectric material in the first layers is formed into a plurality of generally rectangular shapes, the rectangular shapes being evenly distributed within the low acoustic impedance material, and the rectangular shapes in each of the first layers being in alignment with the rectangular shapes in the other first layers when the first layers, the internal electrodes, and the first and second external electrodes are formed into the transducer.

8. A transducer for use in a system generating and receiving ultrasonic sound waves, the transducer comprising:

a plurality of first layers, the first layers comprised of a piezoelectric material dispersed periodically within a low acoustic impedance material;

a plurality of second layers placed between the first layers, the second layers comprising an electrically conductive and mechanically rigid material, the first and second layers being fused together to form the transducer; and a first and second external, electrode coupled alternatively to the second layers.

9. The transducer of claim 8 wherein the piezoelectric material comprises lead zirconate titanate and the low acoustic impedance material comprises a polymer material.

10. The transducer of claim 8 wherein the piezoelectric material in the first layers is formed into structures which comprise one of a plurality of shapes comprising at least rectangular columns, cylindrical columns or rectangular slabs.

11. The ultrasonic transducer of claim 9 wherein the second layers comprise a carbon fiber reinforced composite material.

12. The ultrasonic transducer of claim 10 wherein the second layers comprise a carbon fiber reinforced composite material.

13. The transducer of claim 10 wherein the first layers are formed by injection molding, the second layers comprise a conductive ink, and the first and second layers are sintered together to form the transducer.

14. A ultrasonic transducer:

a plurality of first layers comprising both piezoelectric and polymer materials, the layers together approximating the acoustic impedance of a first test object; and a plurality of second layers, placed between the first layers for reducing unwanted resonances between the first layers.

15. The ultrasonic transducer of claim 14 wherein the first layers are formed by injection molding of the piezoelectric material.

16. The transducer of claim 14 wherein the piezoelectric material of the first layers formed into geometric shapes comprising one of a plurality of geometric shapes comprising cylindrical columns, rectangular columns, and rectangular slabs.

17. The transducer of claim 16 wherein the distance between the geometric shapes defines a pitch and the height of the geometric shapes defines a thickness, the pitch divided by the thickness forming a ratio, the ratio having a value of less than 0.7.

18. The transducer of claim 17 wherein the ratio has a value of less than 0.35.

19. In a multilayer transducer for an ultrasonic diagnostic system, the multilayer transducer comprising at least a plurality of composite piezoelectric layers, a method for reducing and eliminating unwanted acoustic resonances between the composite piezoelectric layers, the method comprising the step of placing an electrically conductive and mechanically rigid material between the composite piezoelectric layers forming the transducer.

20. The method of claim 19 wherein the composite piezoelectric layers are formed by injection molding.

* * * * *